(12) United States Patent
Schmidt et al.

(10) Patent No.: US 7,886,578 B2
(45) Date of Patent: Feb. 15, 2011

(54) SENSOR ELEMENT FOR PARTICLE SENSORS AND METHOD FOR OPERATING THE SENSOR ELEMENT

(75) Inventors: Ralf Schmidt, Gerlingen (DE); Markus Siebert, Leonberg (DE); Sabine Roesch, Ditzingen (DE); Helmut Marx, Hochdorf (DE); Henrik Schittenhelm, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 823 days.

(21) Appl. No.: 11/661,789

(22) PCT Filed: Jul. 18, 2005

(86) PCT No.: PCT/EP2005/053435

§ 371 (c)(1),
(2), (4) Date: Sep. 14, 2007

(87) PCT Pub. No.: WO2006/027288

PCT Pub. Date: Mar. 16, 2006

(65) Prior Publication Data

US 2008/0047847 A1  Feb. 28, 2008

(30) Foreign Application Priority Data

Sep. 7, 2004 (DE) .................. 10 2004 043 121

(51) Int. Cl.
*G01N 15/02* (2006.01)
*G01N 27/60* (2006.01)

(52) U.S. Cl. .................... 73/28.01; 73/31.02; 73/31.03; 73/31.05; 73/31.06

(58) Field of Classification Search .................. 73/23.2, 73/23.31–23.33, 31.01–31.06, 28.01
See application file for complete search history.

(56) References Cited

U.S. PATENT DOCUMENTS

| 4,300,990 | A | * | 11/1981 | Maurer ....................... 204/412 |
| 4,720,394 | A | * | 1/1988 | Kojima et al. ................ 427/102 |
| 5,247,827 | A | | 9/1993 | Shah et al. |
| 6,709,558 | B2 | * | 3/2004 | LaBarge et al. ............. 204/429 |
| 7,543,477 | B2 | * | 6/2009 | Berger et al. ................ 73/23.33 |
| 2001/0035044 | A1 | * | 11/2001 | Larsson et al. ............. 73/28.01 |
| 2001/0051108 | A1 | * | 12/2001 | Schonauer ................. 422/68.1 |
| 2003/0196499 | A1 | | 10/2003 | Bosch et al. |

FOREIGN PATENT DOCUMENTS

| DE | 101 56 946 | 5/2003 |
| DE | 102 19 798 | 11/2003 |
| DE | 103 31 838 | 9/2004 |
| JP | 59-196453 | 11/1984 |
| JP | 59-197847 | 11/1984 |
| JP | 5-2005 | 1/1993 |

* cited by examiner

*Primary Examiner*—David A. Rogers
(74) *Attorney, Agent, or Firm*—Kenyon & Kenyon LLP

(57) ABSTRACT

A sensor element for gas sensors for determining the concentration of particulates in gas mixtures, in particular soot sensors having at least one first measuring electrode applied to an electrically insulating substrate and at least one second measuring electrode, a voltage being applicable to the first and second measuring electrodes. The first measuring electrode is at least partly covered by a porous material open to diffusion of the particles to be determined.

13 Claims, 2 Drawing Sheets

SENSOR ELEMENT FOR PARTICLE SENSORS AND METHOD FOR OPERATING THE SENSOR ELEMENT

FIELD OF THE INVENTION

The present invention is directed to a sensor element and a method for determining the concentration of particulates in gas mixtures, and their use as defined in the preambles of the independent claims.

BACKGROUND INFORMATION

As a result of increasingly strict environmental legislation, exhaust gas treatment systems allowing soot particles existing in combustion exhaust gases to be filtered out or eliminated are gaining in importance. In order to check or monitor the operability of such exhaust gas treatment systems, sensors are needed which allow the instantaneous particulate concentration existing in the combustion exhaust gas to be accurately determined even in extended operation. In addition, sensors of this type should allow the load of diesel particulate filters, for example, provided in an exhaust gas system to be predicted in order to achieve a high degree of system reliability, thus allowing the use of more cost-effective filter materials.

German patent document DE 102 19 798 A1 discusses a sensor for detecting substances in a fluid stream, which is designed on the basis of a ceramic multilayer substrate. It includes two measuring electrodes at a distance from each other which are exposed to the combustion exhaust gas to be studied. If soot deposits between the two measuring electrodes and a voltage is applied to the measuring electrodes, a current will flow between the measuring electrodes. Two layered heating elements make it possible to thermally free the electrodes and their surroundings from deposited soot particles. The sensor also includes a filter which is connected upstream from the measuring gas space containing the measuring electrodes, in the direction of flow of the measuring gas. The upstream filter causes coarse soot particles to deposit when the measuring gas diffuses inside the sensor. The disadvantage of this type of sensors is, on the one hand, the high cost of their manufacture and, on the other hand, the dependence of the obtained measurement results on the particle size distribution of the soot contained in the measuring gas because both the filter load from coarse particles and the measuring electrode load from fine particles influence the measurement result without the possibility of separating the two influences.

An object of the exemplary embodiment and/or exemplary method of the present invention is to provide a sensor element for sensors and a method for determining the particulate concentration in gas mixtures, which exhibits a high degree of accuracy of the obtained measuring signals while being cost-effective.

SUMMARY OF THE INVENTION

The sensor element and the method having the characteristic features of the independent claims have the advantage that they allow the object of the exemplary embodiment and/or exemplary method of the present invention to be achieved in an advantageous manner because of the simple design of the sensor element in particular and because of the use of a porous layer in physical contact with a measuring electrode of the sensor element and open for the diffusion of the particles to be determined, which acts both as a particle trap and as an element for smoothing the gas mixture flow reaching the measuring electrode surface. In particular, the sensor element of the exemplary embodiment and/or exemplary method of the present invention is considerably less sensitive to the deposit of larger soot or other particles affecting the electrical conductivity of the sensor element which, in the case of openly accessible measuring electrodes, may possibly result in a short circuit and sudden signal changes of the sensor element. Another advantage results from the fact that particles which have already diffused into the pores of the porous layer may not be re-entrained by turbulence within the gas mixture to be determined. This improves the stability of the measuring signals of the sensor element.

Other advantageous specific embodiments of the present sensor element and the method for operating the sensor element result from the subclaims.

It is thus advantageous if the measuring electrodes may be intermeshing interdigital electrodes because in this way the electrical resistance, i.e., the electrical conductivity of large surface regions may be determined under defined conditions and thus the sensitivity and quality of the measuring signal may be substantially improved.

Similar advantages are achieved if the measuring electrodes are situated in different layer levels of the sensor element. This makes it possible to design at least one of the measuring electrodes as a flat electrode, so that a large surface of the sensor element is at least largely covered. The arrangement of the measuring electrodes one on top of the other in different layer levels shortens the conductivity path between the measuring electrodes which must be bridged by soot particles. Thus, in the case of ceramic sensor elements, normally only a resolution of approximately 100 μm of the structures is implementable in the lateral direction, while, in contrast, in the vertical direction, the layer thickness of the structures may be 10 μm to 15 μm. By shortening the distance between the measuring electrodes to be bridged by particles, the time period until the triggering threshold of the sensor element is exceeded is shortened by the same measure, so that the sensor element exhibits a substantially better measuring sensitivity in the case of measuring electrodes arranged on top of each other.

In another embodiment of the present invention, the porous layer is made of the same or at least similar material as the substrate onto which at least one of the measuring electrodes of the sensor element is applied. This may be an electrically insulating material such as aluminum oxide, to which alkaline earth oxides are added, for example.

In another embodiment of the present invention, an analyzer device is provided which ascertains a change in the current flow between the measuring electrodes per unit of time and outputs it as a measure of the particulate concentration.

The sensor element and the method for operating the sensor element are advantageously suitable for monitoring the operation of a diesel engine, i.e., for checking the operability or the loading state of a particulate filter.

DETAILED DESCRIPTION

Figure 1A:
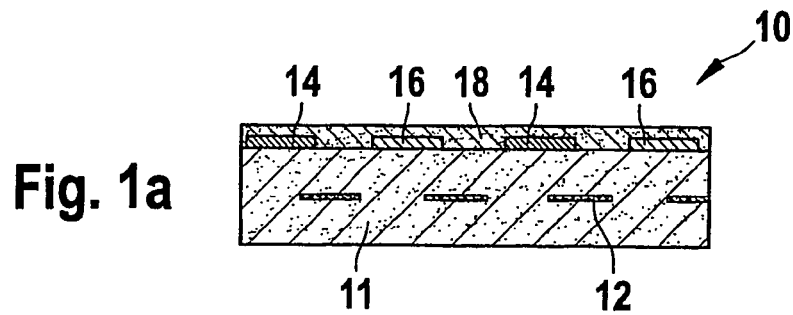
FIG. 1a shows longitudinal sections through sensor elements according to a variant of a first exemplary embodiment.

FIGS. 1a through 1d show a schematic structure of a first specific embodiment of the present invention. Reference numeral 10 denotes a ceramic sensor element for determining a particulate concentration in a gas mixture surrounding the sensor element. Sensor element 10 includes a ceramic substrate 11, an electrically insulating material such as barium-containing aluminum oxide being used as the ceramic material because this material has a largely constant high electrical resistance over a long period of time even when exposed to thermal cycling. Alternatively, the use of cerium dioxide and/or the addition of other alkaline earth oxides is also possible.

Sensor element 10 also has a ceramic heating element 12 which is designed in the form of a resistive printed conductor and is used for heating sensor element 10, in particular to the temperature of the gas mixture to be determined or for burning off the soot particles deposited on the surface of sensor element 10. The resistive printed conductor may be made of a cermet material, which may be as a mixture of platinum or a platinum metal with ceramic components such as aluminum oxide, for example. The resistive printed conductor may be in the form of a meander and has electrical terminals (not depicted) at both ends. By applying an appropriate heating voltage to the terminals of the resistive printed conductor, the heating power of heating element 12 may be appropriately regulated.

Two measuring electrodes 14, 16, for example, designed as intermeshing interdigital electrodes according to FIG. 1a, are applied to a large surface of sensor element 10. The use of interdigital electrodes as measuring electrodes 14, 16 makes it advantageously possible to determine, with particularly high accuracy, the electrical resistance, i.e., the electrical conductivity of the surface material located between measuring electrodes 14, 16. To contact measuring electrodes 14, 16, contact surfaces (not depicted) are provided in the area of an end of the sensor element facing away from the gas mixture.

Furthermore, a porous layer 18, which at least largely covers substrate 11 and shields measuring electrodes 14, 16 against direct contact with the gas mixture to be determined, is provided on the large surfaces of sensor element 10 provided with measuring electrodes 14, 16. The thickness of porous layer 18 may be greater than the thickness of measuring electrodes 14, 16. Porous layer 18 may be designed to have open pores, the pore size being selected in such a way that the particles to be determined in the gas mixture are able to diffuse into the pores of porous layer 18. The pore size of porous layer 18 may be in the range of 2 µm to 10 µm. Porous layer 18 is made of a ceramic material, which may be similar or identical to the material of substrate 11 and may be manufactured in a simple manner by screen printing. The porosity of porous layer 18 may be appropriately adjusted by adding pore-forming agents to the screen printing compound.

During the operation of sensor element 10, a voltage is applied to measuring electrodes 14, 16. Since measuring electrodes 14, 16 are situated on the surface of electrically insulating substrate 11, essentially no current flows between measuring electrodes 14, 16.

If a gas mixture flowing around sensor element 10 contains particulates, in particular soot, these deposit on the surface of sensor element 10. Due to the open-pore structure of porous layer 18, the particles diffuse through porous layer 18 until they reach the immediate proximity of measuring electrodes 14, 16. Since soot has a certain electrical conductivity, if the surface of sensor element 10, i.e., porous layer 18, is loaded with soot to a sufficient degree, an increasing current flow will occur between measuring electrodes 14, 16, which correlates with the amount of load.

If a constant direct or alternating voltage is now applied to measuring electrodes 14, 16, and the increase of current flow over time is ascertained, the instantaneous particulate mass flow in the gas mixture, in particular the soot mass flow, may be inferred from the current flow increase to time quotient. Using this measurement method, the concentration of all those particles in a gas mixture which positively or negatively affects the electrical conductivity of the ceramic material located between measuring electrodes 14, 16 may be detected.

Figure 1B:
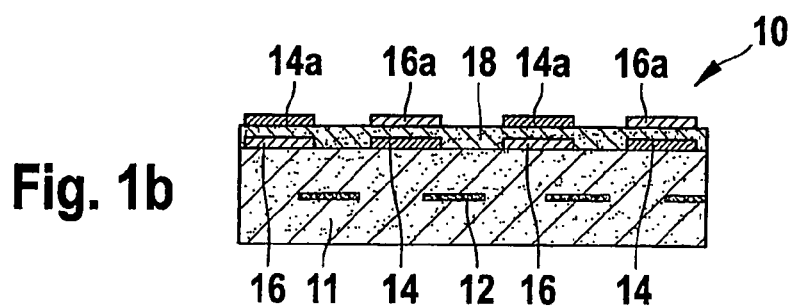
FIG. 1b shows longitudinal sections through sensor elements according to a variant of a first exemplary embodiment.

FIG. 1b shows a variant of the sensor element illustrated in FIG. 1a. The same reference numerals denote the same components as in FIG. 1a.

The measuring electrodes of sensor element 10 depicted in FIG. 1b are situated in two different layer levels of sensor element 10. First measuring electrodes 14, 16 are directly applied to a large surface of substrate 11 and are surrounded by porous layer 18. Additional measuring electrodes 14a, 16a are provided on the additional large surface formed by porous layer 18. Additional measuring electrodes 14a, 16a are not covered by porous layer 18. Measuring electrodes 14, 14a, 16, 16a are designed as interdigital electrodes; for example, measuring electrodes 14, 16, 14a, 16a may be arranged congruently on top of each other. The advantage of this second variant of the first exemplary embodiment is that short distances between measuring electrodes 14, 16a, and 14a, 16 may be implemented in a simple manner, the response behavior of sensor element 10 being improved even at low particulate concentrations.

In addition, with the aid of additional measuring electrodes 14a, 16a, the electrical surface conductivity of porous layer 18 may be easily determined, from which in particular the concentration of the particles present in the gas mixture and having a certain minimum diameter may be determined. If this additional advantage is considered of no value, additional measuring electrodes 14a, 16a may also be coated with another porous protection layer (not depicted), open to diffusion of the particles to be measured.

Figure 1C:
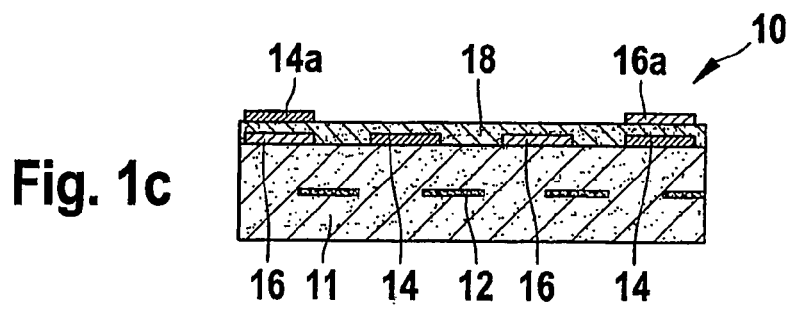
FIG. 1c shows longitudinal sections through sensor elements according to a variant of a first exemplary embodiment.

FIG. 1c shows another variant of the sensor element according to the first exemplary embodiment. The same reference numerals denote the same components as in FIGS. 1a and 1b.

In the third variant depicted in FIG. 1c, additional measuring electrodes 14a, 16a are not designed as interdigital electrodes, but in the form of simple track conductors positioned on porous layer 18. This simplifies the design of sensor element 10 considerably. According to the third variant depicted in FIG. 1d, additional measuring electrodes 14a, 16a may be coated with an additional porous layer 20, which is also designed to be open to diffusion of the particles to be determined and may be, although not necessarily, made of the same material as porous layer 18.

Figure 1D:
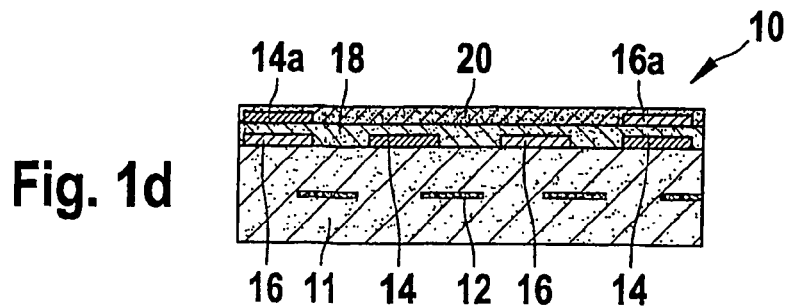
FIG. 1d shows longitudinal sections through sensor elements according to a variant of a first exemplary embodiment.

The particular advantage of the variants depicted in FIGS. 1c and 1d is that even if porous layer 18 has already been saturated with soot deposited within it, the soot subsequently deposited laterally on the surface of porous layer 18 between electrodes 14a, 16a may still be determined.

Figure 2:
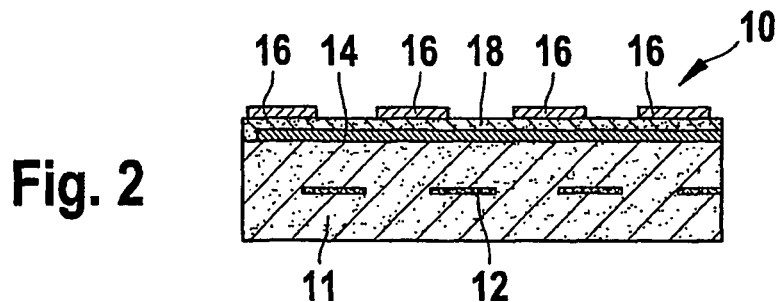
FIG. 2 shows a longitudinal section through a sensor element according to a second exemplary embodiment.

FIG. 2 depicts a sensor element according to a second exemplary embodiment of the present invention. The same reference numerals denote the same components as in FIGS. 1a through 1d.

In the second exemplary embodiment depicted in FIG. 2, measuring electrode 14 has a flat shape, the large surface of sensor element 10 may be at least largely covered. In an additional layer level of the sensor element, measuring electrode 16 is designed in the form of an interdigital electrode on the additional large surface of sensor element 10 formed by porous layer 18.

Figure 3A:
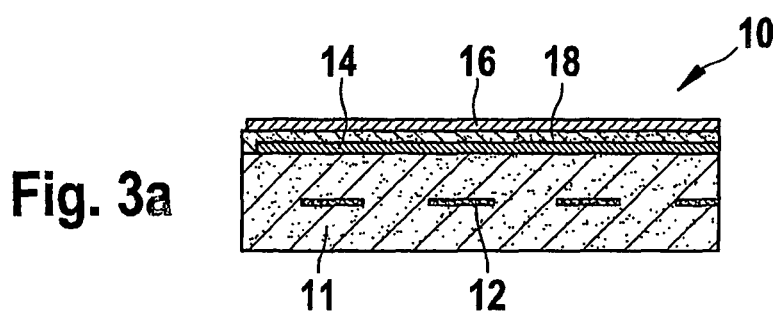
FIG. 3a shows longitudinal sections through sensor elements according to a variant of a third exemplary embodiment.

FIG. 3a depicts a sensor element according to a third exemplary embodiment of the present invention. The same reference numerals denote the same components as in the previously described figures.

Figure 3B:
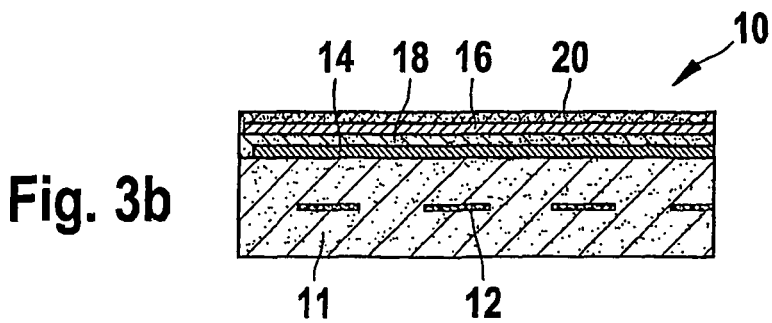
FIG. 3b shows longitudinal sections through sensor elements according to a variant of a third exemplary embodiment.

Sensor element 10 depicted in FIG. 3a has two flat, porous electrodes 14, 16, which are formed in different layer levels of the sensor element and may be positioned congruently on top of each other, fully covering each other. It is, however, also possible to provide measuring electrodes 14, 16 with different geometric designs and/or not to position them congruently. The advantage of this specific embodiment is that the influence of the surface conductivity of porous layer 18 on the measuring signal of sensor element 10 may be ruled out. One variant of sensor element 10 according to the third exemplary embodiment is depicted in FIG. 3b. Here measuring electrode 14 is covered by porous layer 18, and measuring electrode 16 is covered by additional porous layer 20. Additional porous layer 20 protects measuring electrodes 16 against abrasive influences of the gas mixture to be determined.

The present invention is not limited to the specific embodiments of a sensor element depicted in FIGS. 1 through 3, but it may be used in numerous variants of this sensor element. It is thus possible, for example, to provide substrate 11 as a ceramic multilayer structure or to provide additional measuring electrodes.

The use of the above-described sensor element is not limited to the determination of soot particles in exhaust gases of internal combustion engines, but it may be used in general for determining the concentration of particles which modify the electrical conductivity of a ceramic substrate when deposited therein, for example, in chemical manufacturing processes or exhaust air (gas) treatment systems.

What is claimed is:

1. A gas or soot sensor element for determining a concentration of particulates in gas mixtures, comprising:
   at least one first measuring electrode applied to an electrically insulating substrate; and
   at least one second measuring electrode, a voltage being appliable to the first and second measuring electrodes, wherein at least the first measuring electrode is at least partly covered by a porous material open to diffusion of the particles to be determined,
   wherein at least one of the first measuring electrode and the second measuring electrode are situated in different layer levels of the sensor element.

2. The sensor element of claim 1, wherein at least one of the first measuring electrode and the second measuring electrode includes an interdigital electrode.

3. The sensor element of claim 1, wherein the at least one of the first measuring electrode and the second measuring electrode includes a flat electrode at least largely covering a large surface of the sensor element.

4. The sensor element of claim 1, wherein the electrically insulating substrate contains at least one of aluminum oxide and alkaline earth oxides.

5. The sensor element of claim 1, wherein at least one at least one of the first measuring electrode and the second measuring electrode has a porous design.

6. The sensor element of claim 1, further comprising: an analyzer device to determine a change in the current flow between the measuring electrodes per unit of time and outputs it as a measure of the particulate concentration.

7. The sensor element of claim 1, wherein the porous material is formed by or includes the material of the electrically insulating substrate.

8. The sensor element of claim 1, further comprising: a heating element to heat the sensor element to a temperature above a burn-off temperature of the particles to be determined.

9. The sensor element of claim 1, wherein at least one of the first measuring electrode and the second measuring electrode are situated one on top of the other in the different layer levels.

10. The sensor element of claim 1, wherein at least one of the first measuring electrode and the second measuring electrode are both at least partly covered by a porous material.

11. A method for determining a concentration of particulates in a gas mixture with a sensor element, the method comprising:
   applying a voltage to at least two of measuring electrodes of a gas or soot sensor element for determining a concentration of particulates in gas mixtures, the sensor including:
   at least one first measuring electrode applied to an electrically insulating substrate; and
   at least one second measuring electrode, a voltage being appliable to the first and second measuring electrodes, wherein at least the first measuring electrode is at least partly covered by a porous material open to diffusion of the particles to be determined, wherein at least one of the first measuring electrode and the second measuring electrode are situated in different layer levels of the sensor element;
   determining a current flow established between the measuring electrodes;
   determining a change in the current flow occurring between the measuring electrodes per unit of time; and
   outputting the change as a measure of the particulate concentration.

12. The method of claim 11, wherein a regeneration of the sensor element is initiated as soon as the current flow established between the measuring electrodes exceeds a predefined value and/or assumes a constant value for a predefined time period.

13. The method of claim 11, wherein the sensor is used for monitoring one of an operation of a diesel engine, an operability of a particulate filter, and a loading state of the particulate filter.

* * * * *